United States Patent [19]

Ekbladh et al.

[11] 4,445,897

[45] May 1, 1984

[54] CATHETER FOR POSTSURGICAL DRAINAGE

[76] Inventors: Fred V. G. Ekbladh, Pl 178, Särö, Sweden, S-430 40; Hans Tillander, Humlegåardsgatan 3, Göteborg, Sweden, S-412 74

[21] Appl. No.: 383,014

[22] Filed: May 28, 1982

[30] Foreign Application Priority Data

Jun. 9, 1981 [SE] Sweden ............................ 8103617

[51] Int. Cl.³ ........................................... A61M 27/00
[52] U.S. Cl. ..................................... 604/280; 604/43
[58] Field of Search ..................... 604/93, 43, 264–284

[56] References Cited

U.S. PATENT DOCUMENTS 1,045,326  11/1912  Ruflin ................................... 604/43
3,136,316  6/1964   Beall .............................. 604/268 X
3,590,820  7/1971   Nehra et al. ......................... 604/268

FOREIGN PATENT DOCUMENTS 2240026  3/1975  France .
2248057  5/1975  France .

Primary Examiner—Dalton L. Truluck
Attorney, Agent, or Firm—Brumbaugh, Graves, Donohue & Raymond

[57] ABSTRACT

The present invention relates to a catheter intended for postsurgical drainage of a wound area after a surgical incision and particularly such a catheter which is connected to a wound secretion receiver being provided with a vacuo. The catheter is characterized in that it at its front end is provided with at least one slot (6), which extends along the catheter (1), whereby throughopenings (9) are arranged from the bottom of the slot (6) to a lumen (2) arranged centrally in the catheter (1). Using the present invention no suction-in of tissue into the lumen (2) of the catheter (1) will occur but the catheter can be removed without applying any greater force and without obtaining any trauma in the wound.

3 Claims, 3 Drawing Figures

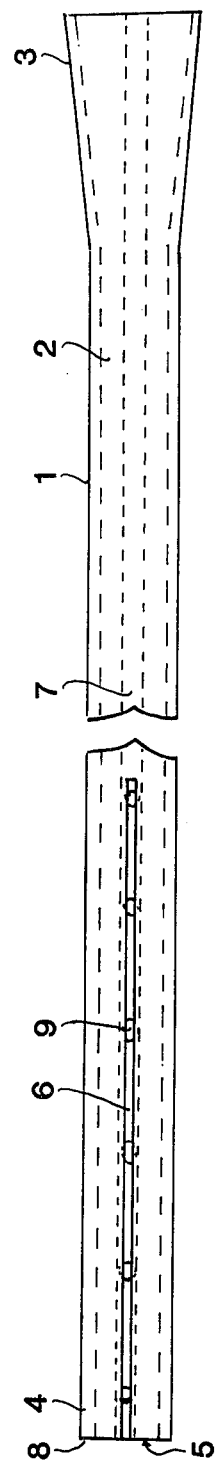
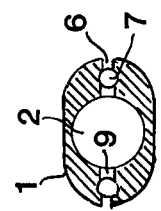
FIG 2
FIG 3

CATHETER FOR POSTSURGICAL DRAINAGE

DESCRIPTION

Technical field

The present invention relates to a catheter for postsurgical drainage of a wound as created by a surgical incision and comprising a tubular, flexible tube having a substantially centrally arranged lumen, which tube in one end is arranged to be connected to a drainage receiving device and in the other end, the front one, to be placed in a wound as created by a surgical incision, the catheter being provided with openings in its front end connecting its outer side with its lumen.

The object of the present invention is to obtain a wound secretion draining catheter into which tissue to be drained is not sucked and which can be removed atraumatically.

BACKGROUND OF THE INVENTION

It is previously known catheters for postsurgical drainage of wound secretion, whereby the catheter tube in its one end, the rear one, is connected to a suction source providing a weak vacuo and with its front end is placed in a wound area, where secretion is formed postsurgically during healing. The catheter is hereby provided with a through-extending lumen and in its front end provided with laterally arranged openings, so called eyes, which are going through the tube wall and through which the secretion is removed by suction. The arrangement of such a secretion drainage has proved to improve healing considerably and thereby reduce the hospital care time, which is positive both to the patients and the society.

It has now, however, been shown that the present type of catheters, having a number of eyes in the sidewalls, causes tissue to be sucked into the lumen, i.a. due to the close proximity of the catheter to the tissue, and expand into the lumen. This further causes, when the catheter is removed, that a very high force, relatively considered, has to be applied to draw the catheter free from the wound area, which causes the formation of a trauma in the wound. The traction power has thereby been measured to 3-4 kp.

In so called surgical aspirators, i.e. aspirators used for removing blood and wound secretion during a pending surgical incision and which aspirators work with high vacuo and high flow rates, it is known to arrange different types of devices to provide for simultaneous passage of air, whereby the suction force is reduced and provides for an atraumatic suction.

Such devices cannot, however, be used in postsurgical wound drainage, as the catheter then is completely embedded in the tissue to be drained and an excess of air is not present.

Further it is known from the prior art, FR No. 2,240,026 and FR No. 2,248,057, a catheter provided with longitudinally extending wide slots, which run either axially or helically and in which slots the eyes are arranged through the walls. These catheters, however, do not solve the problem of an atraumatic removal of the catheter as the tissue will be sucked into the eyes and the lumen to the same extent as if no slots were present.

Prior art, U.S. Pat. No. 3,590,820, further recognizes an aspirator tip comprising a number of longitudinally extending bores, which are connected with the outer surface via a slot, whereby each bore at the very front end of the tip is connected with an inner lumen of the tip by means of a perpendicular bore arranged thereto, i.e. a bore arranged radially from the outer surface of the tip to the inner lumen. The slots and bores are provided in order to obtain a suction of air when the tip is used to remove blood and secretion during a surgical incision, whereby the tip is connected to a high vacuo source. The aspirator tip is only intended for use at surgical incisions and not to be used in postsurgical drainage, where it, if so used, will not give an atraumatical removal due to the radially bores, or passages.

Depending upon the above-mentioned drawbacks, demands have been raised for a catheter for said use which eliminates the suction-in of tissue into the lumen and which makes it possible to considerably reduce, and at least halve the traction power needed at the removal of the catheter, whereby the risk for trauma would be considerably reduced.

DESCRIPTION OF THE PRESENT INVENTION

It has now surprisingly been found possible to overcome these problems by means of a catheter according to the present invention, which catheter is characterized in that it at its front end and in its wall is provided with at least one longitudinally extending slot, whereby the slot is radially widening to the formation of a second lumen from which throughopenings to the inner lumen of the catheter are arranged.

According to a preferred embodiment of the invention the catheter is provided with two slots arranged diametrically opposite to each other.

According to another preferred embodiment of the invention the second lumen extends along the whole catheter to the very front end thereof.

According to another preferred embodiment of the invention the lumen, which is formed by the widening of the slot runs as a lumen parallel to the inner lumen of the catheter and is arranged to allow passage to the area outside the wound area, whereby this second lumen is further arranged to be closed.

Other preferred embodiments of the invention will be evident from the following and the accompanying claims.

By means of the present invention the following is obtained, vis: that the tissue is not sucked into the drainage openings and that the catheter can be removed using a very small force. It has been shown that in most cases the necessary traction power is only 0.3-0.4 kp, and even down to 0.1-0.2 kp.

BEST MODE OF CARRYING OUT THE INVENTION

The present invention is described more in detail with reference to the attached drawings, wherein FIG. 1 shows a perspective view of a preferred embodiment of the invention;

FIG. 2 shows a lateral view of the embodiment of FIG. 1; and

FIG. 3 shows the same embodiment in cross-section.

Figure 1:
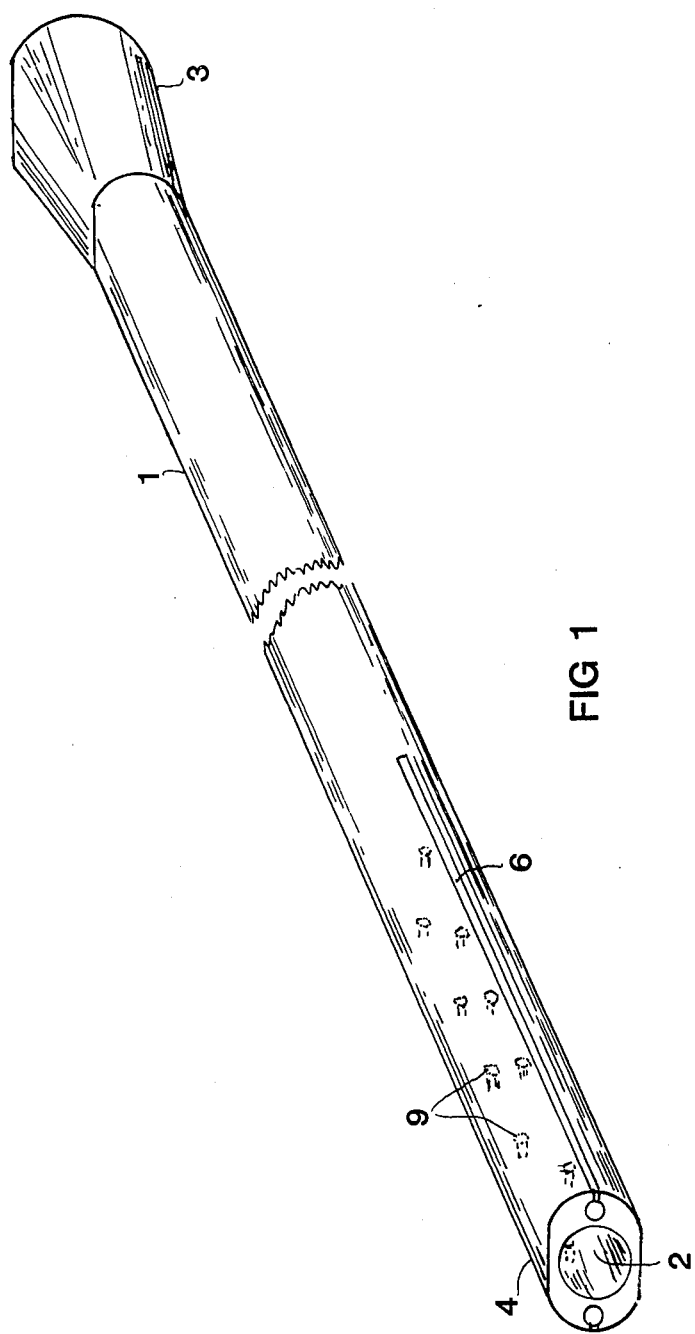

With reference to FIGS. 1 and 2, 1 denotes a catheter provided with a through lumen 2. In the one end of the catheter, the rear one, it is conically designed to be applicable on a connector to a suction source (not shown), for example a bellow suction device, as a DREVAC (reg. Trade Mark). The rear end is denoted 3. The through-extending lumen 2 of the catheter 1 ends in the front end 4 of the catheter in a common circular opening 5. This can, however, if so desired, be closed. From a production-technical point of view, however, it can be economical to leave it open. The catheter 1 is manufactured in any soft and flexible material suited for the purpose, such as polyvinylchloride, ethylene-vinylacetate, silicon elastomer, or latex. The tube material can also preferably be provided with a hydrophilic coating, such as a polyvinylpyrrolidone coating or a polyacrylate coating, which gives the catheter a very low friction when it has been wetted with an aqueous liquid. Other hydrophilic coatings are also available. Further, the catheter can be provided with a coating of heparine for the elimination of the formation of thrombosis.

The catheter, according to FIGS. 1 and 2, is further at its front end 4 provided with two slots 6, which are situated diametrically opposite to each other on each side of the lumen 2 of the catheter 1. The slots 6 have a slot width of about 0.4 mm but can of course be varied with regard to where in the body it is to be used. The slots 6 widens inwardly into each tubular lumen 7, which continue up through the catheter 1 and ends in the rear end of the catheter. These two lumens 7 of the slots 6 are normally closed at the upper end, the rear end, but can if so desired, e.g., for the administration of a drug, be open, or administration can take place through its closure. The two lumens 7 thus run in the wall of the catheter 1 on each side of its inner lumen 2. The slots 6 are normally about 100 mm long and extend all the way down to the very front end 8 of the catheter 1. In the bottom of the slots 6, i.e., its inner wall, a number of throughopenings 9 are arranged, which connect the slots 6 with the inner lumen 2 of the catheter 1 and through which secretion from the wound into which it has been inserted can be sucked by means of the vacuo applied to the inner lumen 2 of the catheter 1, as above mentioned. The openings 9 are placed about 25 mm from each other in each slot 6, i.e. about 5 openings in each slot.

The number of slots 6 can of course be varied from one and upwards depending upon the diameter of the catheter 1 but is in the normal case two to four, preferably two.

The slots 6 do not have to extend to the very front end of the catheter 1 but can end closely above this. The slots are not sharply cut but slope from their bottoms up towards the surface of the catheter 1. This is done in order to provide less possible resistance when the catheter 1 is drawn out of a wound area after healing and tissue is possibly present in each slot 6.

Using the present invention it has been shown that tissue is not sucked into the inner lumen of the catheter and only sucked in a small amount into the slots. Any tissue present in the slots will also move easily in the slots and is set free at the front end of the catheter little by little as the catheter is drawn out. Any trauma will thus not occur.

The width of the slot(s) has above been said to be about 0.4 mm. This width can, however, be varied with regard to the use of the catheter and can vary from 0.1 to 0.6 mm, completely depending upon the place and type of tissue.

The cross-sections of the catheters of the present invention can be varied. As shown above it can take the form of an oval, which of course is technically most preferred as then the amount of material used for the manufacture of the catheter is reduced, which in turn gives the best flexibility to the catheter. However, the catheter can have any cross-section such as a circular or eliptic.

We claim:

1. A catheter for post-surgical drainage of a wound comprising a flexible tube having a distal end and a proximal end, and having a centrally arranged inner lumen extending longitudinally thereof, said catheter being adapted to be connected at its proximal end to a suction means for withdrawing drainage through said lumen and further being adapted for its distal end to be implanted in the wound area to be drained, in which catheter there is provided at least one longitudinal slot opening in the surface of the distal end of said catheter which connects to a second longitudinal lumen which is at least as long as said slot opening and has a maximum width which is larger than the width of said slot opening, and there further being a plurality of through-openings extending between the base of said second lumen into said first lumen, whereby drainage can pass from the wound area to said second lumen, then into said first lumen.

2. Catheter according to claim 1, characterized in that it is provided with two slots (6) arranged diametrically opposite to each other.

3. Catheter according to claim 1, characterized in that the lumen (7) formed by the widening of the slot (6) runs parallel to the inner lumen (2) of the catheter (1) and is arranged to allow passage to the area outside the catheter (1), whereby this second lumen (7) is preferably arranged to be blocked at the rear end of the catheter (1).

* * * * *